United States Patent [19]
Tabuchi et al.

[11] 4,235,241
[45] Nov. 25, 1980

[54] ELECTRODES FOR LIVING BODY

[75] Inventors: Katsuhiko Tabuchi, Chiba; Toshiaki Kato, Ichikawa, both of Japan

[73] Assignee: TDK Electronics Co., Ltd., Tokyo, Japan

[21] Appl. No.: 939,856

[22] Filed: Sep. 5, 1978

[30] Foreign Application Priority Data

Sep. 8, 1977 [JP] Japan .................. 52-108201
Feb. 9, 1978 [JP] Japan .................. 53-13996
Feb. 10, 1978 [JP] Japan .................. 53-14329

[51] Int. Cl.³ .............................. A61B 5/04
[52] U.S. Cl. .................. 128/639; 252/507; 252/520
[58] Field of Search .................. 128/639–644, 128/783–789, 798, 802, 803; 252/520, 507

[56] References Cited

U.S. PATENT DOCUMENTS

| | | | |
|---|---|---|---|
| 3,372,107 | 3/1968 | Klein | 252/520 |
| 3,572,323 | 3/1971 | Yuan | 128/640 |
| 3,743,538 | 7/1973 | Mungaard | 252/520 X |
| 3,752,151 | 8/1973 | Robichaud | 128/641 |
| 3,928,244 | 12/1975 | Passmore | 252/520 |
| 3,976,055 | 8/1976 | Monter et al. | 128/640 |

*Primary Examiner*—Lee S. Cohen
*Attorney, Agent, or Firm*—Brisebois & Kruger

[57] ABSTRACT

An improved electrode for living body is proposed which is excellent in the stability and reliability in detecting and transmitting the electric signals generated in a living body by the physiological electric phenomena such as electrocardiographic, electromyographic and electroencephalographic signals.

The electrode of the invention is characterized by the material which is mainly a titanium hydride or a mixture of a titanium hydride with silver chloride optionally combined with a metal salt with basicity and a carbon powder, e.g. graphite.

11 Claims, 5 Drawing Figures

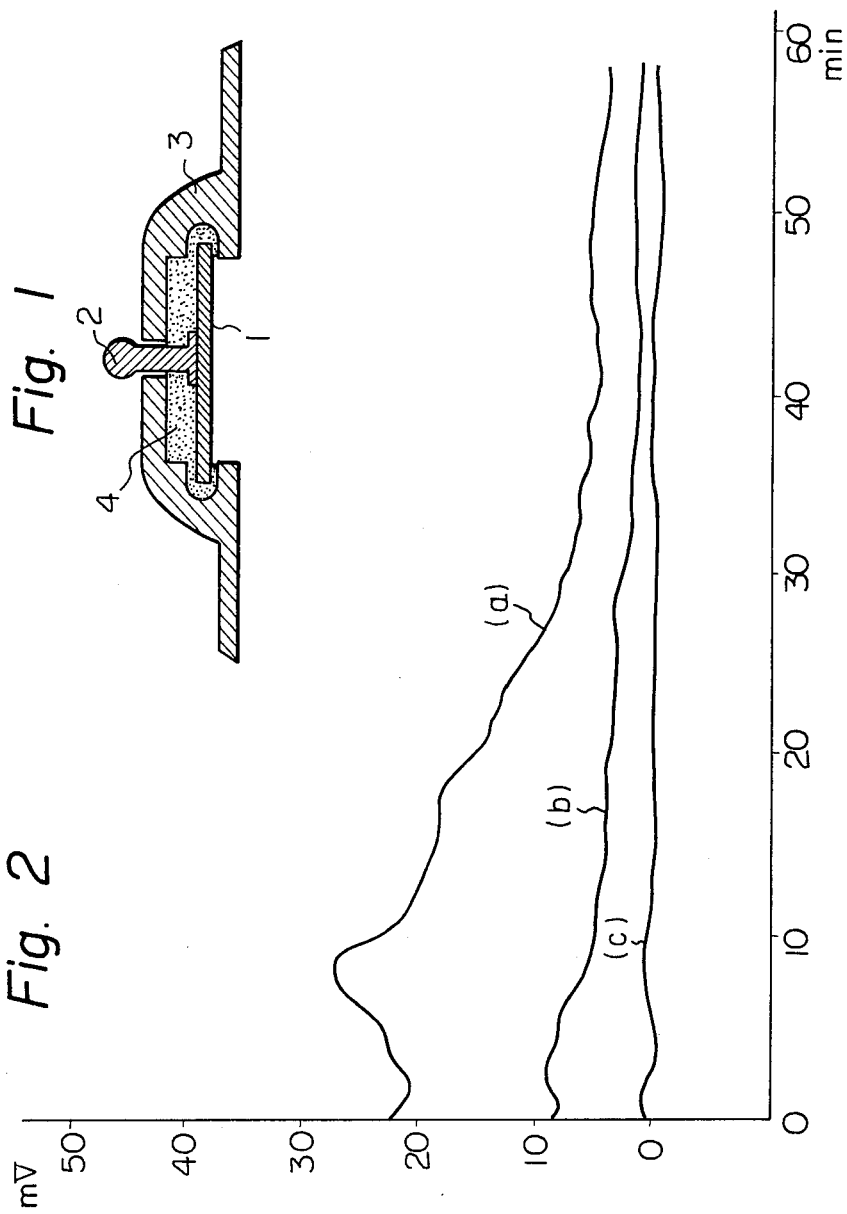

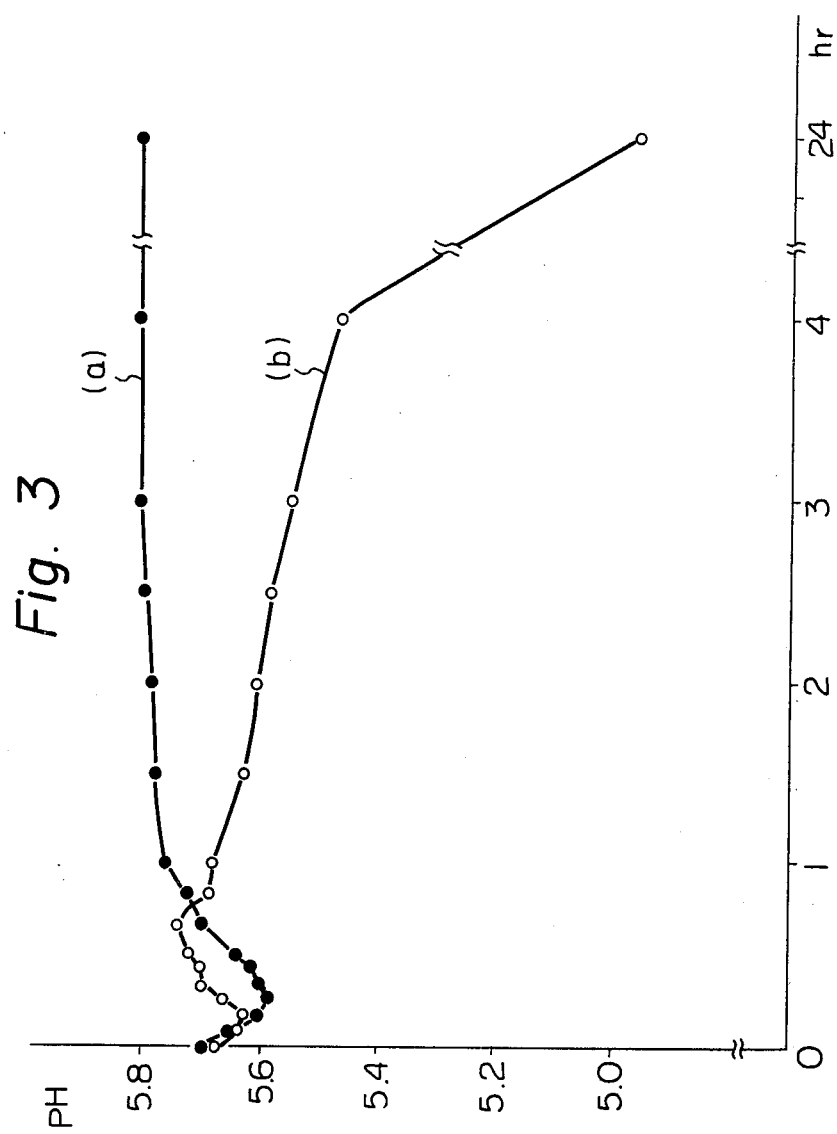

Fig. 5
(a)
(b)
(c)
(d)
(e)

ELECTRODES FOR LIVING BODY

BACKGROUND OF THE INVENTION

The present invention relates to an electrode for living body which is mounted on the skin of a patient to detect the electric signals generated by the physiological electric phenomena taking place in a living body such as electrocardiographic signals, electromyographic signals electroencephalographic signals and the like. In particular, the invention relates to the material of such electrodes for living body capable of very reliable performance.

At the present time, there is a large demand for the measurement and recording of the physiological electric phenomena such as electrocardiograms and electroencephalograms not only in the medical science but also in the fields of biophysics and bioengineering. In these measurements, the role played by the electrodes is very important in order to detect the weak electric signals generated in the living body and to serve as a medium to transmit the signals to the measuring instruments.

Various types of electrodes are used in recent times in order to obtain reliable performance which depends largely upon the construction and material of the electrode. It is the basic requirement that the fluctuation of the electrode potential caused by some phenomena other than the objective electric signals from the living body and the generation of noise can be minimized in order to detect the electric signals accurately and transmit the signals to the measuring instrument when the electrode is mounted on the skin of the living body because the electric signals generated in a living body cannot be so high as exceeding 1 mV or so at highest.

Living bodies are filled with a tissue liquid which can be simulated with the physiological sodium chloride solution, i.e. aqueous solution of sodium chloride in a concentration of 0.9%. Therefore an electrode mounted on a living body to detect the electric signals from the living body and to transit the signals can be simulated approximately by the electrode immersed in an aqueous electrolyte solution which is a 0.9% sodium chloride solution to detect the electric signals from a living body passing through the electrolyte solution and transmit them.

In this case, accurate detection and transmission of the electric signals from a living body require electrode characteristics of the stability in the electrode potential, small impedance of the electrode and the absence of the noise voltages. The fundamental condition to satisfy these requirements is the electrode reaction with good reversibility taking place on the electrode which behaves as a non-polarizable electrode.

Notwithstanding the above requirements, conventional electrodes for living body made of metals such as gold, platinum, silver, tungsten, molybdenum, copper, stainless steel and the like suffer from very large fluctuation in the electrode potential amounting to several tens or hundreds of millivolts in most cases. Thus metal electrodes for living body are never satisfactory for practical use in accurately detecting and transmitting the electric signals from a living body.

In a metal electrode in contact with the liquid in living tissue, i.e. an electrolyte solution, a stable and reversible electrode reaction can hardly be expected to establish the potential of the metal electrode against the solution due to the lack of the free exchange of ions and electrons between the phases of the metal electrode and the electrolyte solution. This situation leads to the unstable potential of the electrode and, particularly immediately after mounting of the electrode to the skin of a living body, to a very remarkable fluctuation in the potential to be stabilized at a relatively constant level only after a lapse of considerable length of time to a great drawback in practical use of the electrode.

As a remedy for the above described defects in metal electrodes for living body, an improved electrode material of silver chloride/silver is known. The performance of this type of the electrode is based on the mechanism that the electrode reaction to establish the electrode potential expressed by the equation $AgCl+e^- \rightleftarrows Ag+Cl^-$ takes place reversibly and with stability so that the exchange of electrons and ions proceeds freely at the interface between the electrode and the electrolyte solution by this reaction giving rise to a relatively stable characteristics of the electrode potential without remarkable polarization.

The silver chloride/silver electrodes above mentioned are prepared typically either by the method of electrolysis conducted in a sodium chloride solution with a silver plate as the anode to deposit a film of silver chloride on the surface of the silver plate or by the method of press molding of a mixture of metallic silver powder and silver chloride powder into a shape of an electrode plate.

The former method, by which most of the commercially available silver chloride/silver electrodes are prepared, has a great difficulty in obtaining uniform film of silver chloride on the surface of the silver plate so as that a stable characteristics of the electrode potential can hardly be expected.

On the other hand, the latter method for the preparation of silver chloride/silver electrodes is disadvantageous from the practical standpoint because of the handling of chemically unstable silver chloride liable to decomposition or denaturation, especially, under the influence of light necessitating special care in the storage and handling of the electrodes.

In addition, the silver chloride/silver electrodes are economically disadvantageous in any way because of the expensiveness of silver and silver chloride as the materials and not suitable as disposable electrodes of wide prevalence with rapidly growing demand in recent years. Thus the electrodes of this type are also excluded from practical use with economy.

SUMMARY OF THE INVENTION

It is therefore an object of the present invention to provide an electrode for living body with excellent electrode characteristics free from the above described problems in the prior art electrodes and with less expensiveness suitable for use as a diposable electrode.

Thus the present invention relates to an improvement in an electrode for living body constructed with an electrode plate having on the upper surface thereof a contact terminal to be connected to a measuring instrument by a lead wire and having the lower surface thereof as exposed bare, which is mounted on a cavity of a dish-like casing, that the electrode plate is made of a titanium hydride as the main constituent which is shaped by press molding into a plate.

In further improved embodiments of the invention, the material of the electrode plate is a mixture of a titanium hydride admixed with a minor amount of silver chloride optionally combined with a metal salt with basicity, and a powder of carbon, e.g. graphite.

BRIEF DESCRIPTION OF THE DRAWING

FIG. 1 is a cross sectional view of the electrode for living body according to the present invention.

FIG. 2 shows the characteristic curves of the electrode potential, in which Curve (a) is for a conventional electrode for living body and Curves (b) and (c) are for the electrodes for living body according to the present invention.

FIG. 3 shows the values of pH of water in which the electrode for living body was dipped taken over a length of time. Curve (a) is for the electrode for living body prepared in Example 4 and Curve (b) is for the electrode for living body prepared in Example 2.

FIG. 5 shows the electrocardiograms taken with the electrodes for living body. Curve (a) was taken with a conventional electrode for living body and Curves (b) to (e) were taken with the electrodes for living body prepared in the Examples of the present invention. In each of the electrocardiograms, the left side is for the patient in rest and the right side is for the same patient under a load of running exercise.

DETAILED DESCRIPTION OF THE PREFERRED EMBODIMENTS

Figure 4:
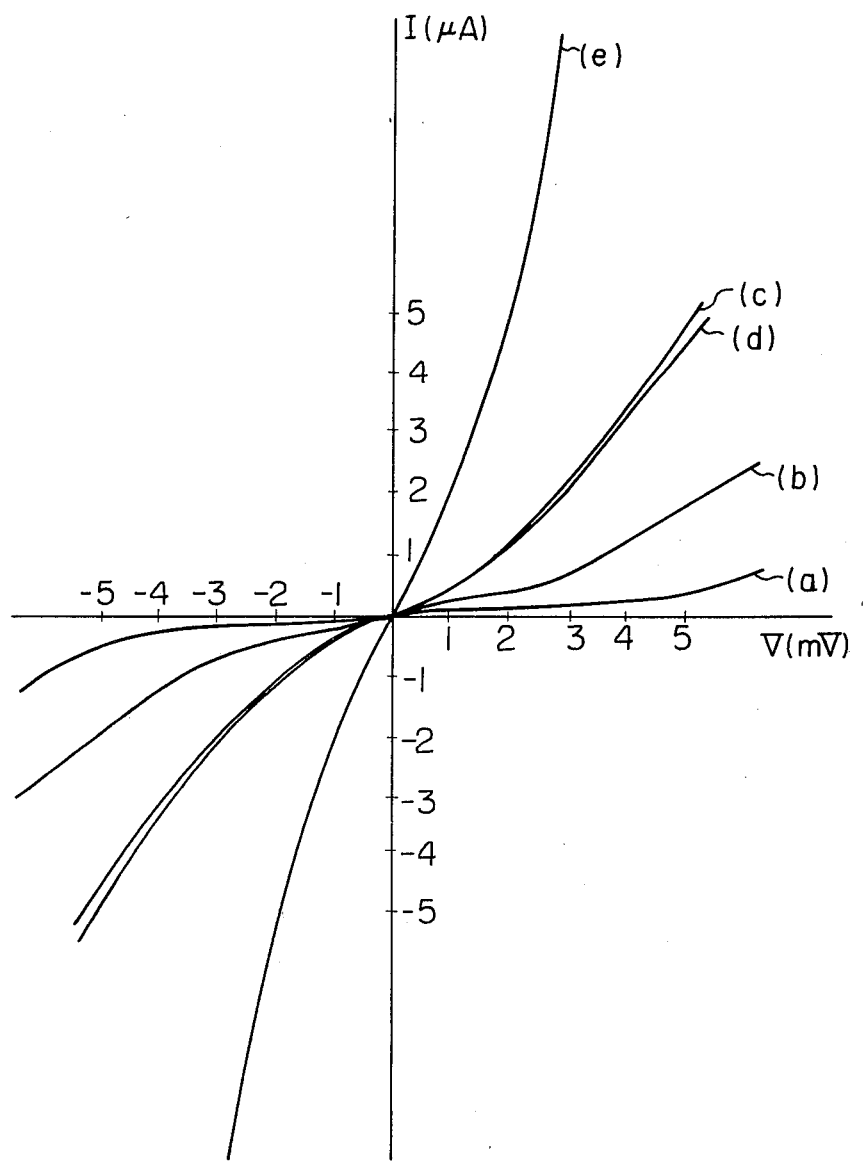
FIG. 4 shows the voltage-current characteristic curves taken by DC voltage application. Curve (a) is for a conventional electrode for living body and Curves (b) to (e) are for the electrodes for living body prepared in the Examples of the present invention.

The structure of the electrode for living body as the objective of the present invention is illustrated with reference to FIG. 1.

FIG. 1 shows the cross section of the electrode for living body, in which 1 is an electrode body with contact terminal 2 attached to the upper surface thereof by welding or adhesion with an electroconductive adhesive, which is connected to a measuring instrument, e.g. an electrocardiograph (not shown), by means of a cord and a connector. The electrode plate 1 is set in the cavity of a dish-like casing or support 3 made of an elastic insulating material such as a plastic or a synthetic rubber by insertion or adhesive bonding with its lower surface exposed bare facing downwardly. The space formed between the upper surface of the electrode plate 1 and the covering portion of the casing 3 is filled with a resin mold 4.

The electrode for living body with a structure as described above is used by being attached to the skin of a living body to an appropriate portion of the body such as the breast and the head of the patient according to the object of the measurement with the lower surface of the electrode plate facing the skin and the cavity formed between the electrode plate and the skin being filled with an electroconductive cream impregnated, for example, with a sodium chloride solution.

Titanium hydrides are good electric conductors and, as has been established by the experiments undertaken by the inventors for the measurements of the electrode potentials, an electrode made of a titanium hydride can operate reversibly and with good stability as an electrode for detecting very weak electric current when in contact with the skin of a living body.

Titanium hydrides are solid solutions of atomic hydrogen interstitially absorbed in the crystalline lattice of metallic titanium with varied degree of hydrogenation up to 2 at the highest corresponding to the composition of $TiH_2$.

The titanium hydride used in the present invention may have any degree of hydrogenation ranging from 1 to 2 as is understood from the working principles but it is recommendable that the degree of hydrogenation is as high as possible in order to ensure better performance of the electrode made thereof.

It was quite out of expectation that a titanium hydride was an ideal material for the electrode for living body since there had been absolutely no information on the use of titanium hydrides as the material for electrodes of any kinds. Further, additional advantages are obtained by the non-expensiveness of titanium hydrides as well as the excellent moldability of titanium hydride powders by press molding into electrode plates of any desired practical shaped such as discs and the like. Thus an electrode plate with sufficient mechanical strengths can be obtained by press molding of a titanium hydride powder with a pressure of about 1 ton/$cm^2$ or more in a suitable metal mold.

Furthermore, advantages are obtained by the chemical stability and the physiological inactivity of the material that no problems of toxicity arise even by prolonged use of the electrode as attached to the skin of a living body or no troubles are encountered as in several of the commercially available electrodes for living body by the formation of rust and deterioration of the electrode performance due to the accumulation of the products by the electrode reactions.

Although the electrode plates shaped with a titanium hydride alone behave excellently with improved electrode characteristics, it is noteworthy that further improvements can be obtained by the electrode plates shaped with a mixture of a titanium hydride admixed with certain additives.

Various compounds have been tested as an additive to improve the behavior of titanium hydride electrodes with a conclusion that the most effective is silver halides, e.g. silver chloride. Thus, 100 parts by weight of a titanium hydride is admixed with 1 to 100 parts by weight or, preferably, 5 to 50 parts by weight of silver chloride intimately by a suitable mixing means to form a powder blend which is shaped into electrodes in the same manner as in the fabrication of the electrodes with a titanium hydride alone. The above given range of the amount of the silver halide is determined in consideration of the moldability of the powder blend as well as the electric conductivity of the shaped electrodes.

It has been further established that the effectiveness of a silver halide, e.g. silver chloride, to improve the characteristics of the titanium hydride electrodes can be enhanced when silver chloride is combined with a metal salt having basicity to exhibit alkalinity in water such as basic salts of alkali metals, e.g. lithium, sodium and potassium and alkaline earth metals, e.g. calcium and magnesium, exemplified by their tungstates, molybdates, sulfites, phosphates, pyrophosphates, hypophosphites, metaphospates, silicates, metasilicates, tetraborates and metaborates as tabulated below in Table 1, in which these salts are classified into three grades A, B and C according to the preference in the present invention, the salts of the groups A with little solubility in water being most preferred and the salts of the group C being less preferred.

TABLE 1

|  | Lithium | Sodium | Potassium | Calcium | Magnesium |
|---|---|---|---|---|---|
| Tungstate | C | A | B | A | A |
| Molybdate | C | A | B | A | A |
| Sulfite | C | B | B | B | B |
| Phosphate | B | B | B | B | B |
| Pyrophosphate | C | B | B | B | B |
| Hypophosphite | C | B | B | B | B |
| Metaphosphate | C | B | B | B | C |
| Silicate | C | B | B | A | A |
| Metasilicate | B | B | B | A | A |
| Tetraborate | A | A | A | A | A |
| Metaborate | C | B | B | C | C |

The amount of these additives to be admixed with the titanium hydride in combination with silver chloride is not limitative insofar as the moldability of the mixture and the electroconductivity of the shaped electrode plate are not affected adversely. Usually it is recommended that from 2 to 25 parts by weight of the basic metal salt are admixed with 100 parts by weight of titanium hydride in consideration of the moldability of the powder mixture, the electroconductivity of the shaped electrode plate and the production cost.

The addition of these additives, either singly or as a mixture of two or more, to titanium hydride brings about further improvements in the reversibility of the electrode reaction, stability of the electrode potential and the non-polarizability of the electrode leading to better performance of the electrode.

In particular, an electrode plate shaped with a mixture of titanium hydride and silver chloride was found to be defective, though with the above mentioned improvements ensured satisfactorily, because of the formation of hydrogen chloride in storage or during use which might be undesirable for a living body. The formation of hydrogen chloride from this type of electrode plates is accelerated at an elevated temperature to which the electrodes may be exposed unavoidably during storage and transportation to cause troubles in later use of them. The mechanism of the formation of hydrogen chloride in the silver chloride-admixed titanium hydride electrode plate is presumably the reaction of hydrogen released thermally from the titanium hydride with the silver chloride.

The use of an additive which is a mixture of silver chloride and a basic metal salt is effective in preventing above described adverse effect caused by the hydrogen chloride, which otherwise is unavoidable, owing to the conversion of the free hydrogen chloride into a material inactive to the living body by the reaction with the basic metal salt.

The advantageous effects of a combined additive of silver chloride and a basic metal salt can be further enhanced by the additional admixture of carbon powder to give further improved reversibility of the electrode reaction and polarization characteristics.

Namely, an electrode plate shaped with titanium hydride admixed with silver chloride, a basic metal salt and carbon powder satisfies all of the requirements for an electrode for living body with very little noise formation and very small drift of the base line because the electrode plate behaves as a non-polarizable electrode with stable (static) electrode potential owing to the very good reversibility of the electrode reaction.

The carbon powder suitable for use as a component of the above additives may be either amorphous carbon or graphite if a sufficiently high purity is ensured and is not limited by the method of its manufacture.

The recommended formulation of the mixture for electrode plate when a carbon powder is admixed is such that from 1 to 100 parts by weight or, more preferably, from 5 to 50 parts by weight of silver chloride, from 1 to 50 parts by weight or, more preferably, from 2 to 25 parts by weight of the basic metal salt and from 1 to 20 parts by weight or, more preferably, from 1 to 10 parts by weight of the carbon powder are admixed with 100 parts by weight of the titanium hydride in consideration of the moldability, electroconductivity and the production cost.

The electrode characteristics of the inventive electrode for living body are so excellent that the measurement can be performed for a patient not only in a rest state but also under exercise load continuously for a prolonged time of period with very little fluctuation in the electrode potential, very small base line drift and little mixing of noise to give very stable and reliable recording of measurement. In addition, the non-expensiveness of the inventive electrode can give disposability to the electrodes to be of great practical value.

Following are the examples and a control to illustrate the inventive electrode for living body in further detail.

EXAMPLE 1

A commercial grade titanium hydride in a form of powder having a composition corresponding to $TiH_{1.924}$ was used as the material for electrode and 0.2 g of the powder was press-molded under a pressure of 3 tons/cm$^2$ into a disc of 10 mm diameter.

An electrode for living body as shown in FIG. 1 was assembled with the above prepared disc as the electrode plate. The terminal of the lead wire was bonded to the electrode plate with an electroconductive adhesive and a silicone resin was used as the mold.

The characteristics of the electrode potential was examined by measuring the potential difference between the terminals of two electrodes for living body prepared as described above, which were bonded at the brims thereof with the electrode plates facing each other and the cavity between two electrode plates being filled with cotton wet with a 0.9% aqueous sodium chloride solution. The measurement was continued for 24 hours and the results are summarized in Table 2 below for 10 pairs of the electrodes for living body. The data for one of the electrode pairs in Table 2 were plotted in Curve (b) of FIG. 2 for a time period of 60 minutes from the beginning.

For comparison, the same measurement procedure was undertaken with 10 pairs of conventional nickel silver electrodes and the data are shown in Table 3 and by Curve (a) in FIG. 2, with the potential difference in millivolts as the ordinate and the time of measurement in minutes as the abscissa.

TABLE 2

| Electrode pair No. | Potential Difference between Electrodes, mV | | | | | | |
|---|---|---|---|---|---|---|---|
|  | Initial | After 1 min. | After 10 mins. | After 30 mins. | After 1 hr. | After 10 hrs. | After 24 hrs. |
| 1 | 7.4 | 6.6 | 8.3 | 7.1 | 6.2 | 5.6 | 3.7 |
| 2 | 8.2 | 11.8 | 6.6 | 7.7 | 5.6 | 4.0 | 5.8 |
| 3 | 2.9 | 8.2 | 8.8 | 7.9 | 7.2 | 8.4 | 6.3 |
| 4 | 5.1 | 2.3 | −1.6 | −2.4 | −0.3 | 4.5 | 5.2 |
| 5 | 0.8 | −3.6 | −5.7 | −2.2 | −3.8 | −2.7 | −1.4 |
| 6 | 10.2 | 12.4 | 7.6 | 5.8 | 3.0 | 3.5 | 4.7 |
| 7 | 8.3 | 8.1 | 7.2 | 5.3 | 3.9 | 2.6 | 0.8 |

TABLE 2-continued

| Electrode pair No. | Potential Difference between Electrodes, mV | | | | | |
|---|---|---|---|---|---|---|
| | Initial | After 1 min. | After 10 mins. | After 30 mins. | After 1 hr. | After 10 hrs. | After 24 hrs. |
| 8 | 4.4 | 0.5 | −0.8 | −2.2 | −1.0 | 0.7 | −1.3 |
| 9 | 1.1 | −0.4 | 1.6 | 3.7 | 5.4 | 3.3 | 2.6 |
| 10 | 9.2 | 11.5 | 13.8 | 8.4 | 7.7 | 6.2 | 3.9 |

TABLE 3

| Electrode pair No. | Potential Difference between Electrodes, mV | | | | | |
|---|---|---|---|---|---|---|
| | Initial | After 1 min. | After 10 mins. | After 30 mins. | After 1 hr. | After 10 hrs. | After 24 hrs. |
| 1 | 23.7 | 18.7 | 27.3 | 23.2 | 14.6 | 12.5 | 13.8 |
| 2 | 26.5 | 39.2 | 43.3 | 25.1 | 14.5 | 20.6 | 15.0 |
| 3 | 74.6 | 66.7 | 35.8 | 51.9 | 24.8 | 17.3 | 9.6 |
| 4 | 15.5 | 4.2 | −19.6 | −22.6 | −34.4 | −28.0 | −7.2 |
| 5 | 46.5 | 39.8 | 14.3 | 7.7 | 12.8 | 25.2 | 18.6 |
| 6 | 62.7 | 70.5 | 36.2 | 18.4 | 8.1 | 11.6 | 4.3 |
| 7 | 7.4 | 12.6 | 28.5 | 2.2 | −1.6 | 4.8 | 6.5 |
| 8 | 0.6 | −1.1 | 18.8 | 20.6 | 9.4 | 5.3 | −6.7 |
| 9 | 16.5 | 23.5 | 22.2 | 15.4 | 19.0 | 18.1 | 7.5 |
| 10 | 38.3 | 33.8 | 16.0 | 8.7 | 5.3 | 1.1 | −3.4 |

EXAMPLE 2

Electrode plates were prepared by press-molding a powder mixture of 100 parts by weight of the same titanium hydride as used in Example 1 and 10 parts by weight of a reagent grade silver chloride and electrodes for living body were obtained in the same manner as in Example 1.

The electrode potential characteristics of these electrodes for living body were examined as in Example 1 and the results are shown in Table 4 and by Curve (c) in FIG. 2. As is evident from these results, the addition of silver chloride is remarkably effective in stabilizing the electrode potential.

TABLE 4

| Electrode pair No. | Potential Difference between Electrodes, mV | | | | | |
|---|---|---|---|---|---|---|
| | Initial | After 1 min. | After 10 mins. | After 30 mins. | After 1 hr. | After 10 hrs. | After 24 hrs. |
| 1 | 1.15 | 0.87 | 0.63 | 0.38 | 0.24 | 0.13 | 0.08 |
| 2 | 0.62 | 0.59 | 0.51 | 0.37 | 0.23 | 0.16 | 0.08 |
| 3 | 0.44 | 0.43 | 0.36 | 0.27 | 0.30 | 0.12 | 0.09 |
| 4 | 0.83 | 0.75 | 0.59 | 0.42 | 0.31 | 0.25 | 0.14 |
| 5 | 0.06 | 0.01 | −0.47 | −0.22 | −0.25 | −0.18 | −0.04 |
| 6 | 0.83 | 0.77 | 0.38 | 0.45 | 0.35 | 0.30 | 0.14 |
| 7 | 0.51 | 0.66 | 0.42 | 0.34 | 0.17 | 0.07 | 0.10 |
| 8 | 0.45 | 0.43 | 0.32 | 0.28 | 0.11 | 0.13 | 0.06 |
| 9 | 0.70 | 0.62 | 0.40 | 0.31 | 0.18 | 0.11 | 0.05 |
| 10 | 0.55 | 0.53 | 0.35 | 0.27 | 0.22 | 0.14 | 0.12 |

EXAMPLE 3

The experimental procedure was the same as in Example 2 except that the amount of silver chloride was varied in the range from 1 part by weight to 100 parts by weight per 100 parts by weight of the titanium hydride. The results are summarized in Table 5 below, in which each of the numerical values is an average for 10 pairs of the electrodes for living body.

TABLE 5

| Silver chloride, parts by weight | Potential Difference between Electrodes, mV | | | | | |
|---|---|---|---|---|---|---|
| | Initial | After 1 min. | After 10 mins. | After 30 mins. | After 1 hr. | After 10 hrs. | After 24 hrs. |
| 1 | 0.87 | 0.79 | 0.66 | 0.58 | 0.32 | 0.30 | 0.21 |
| 5 | 0.58 | 0.55 | 0.36 | 0.29 | 0.23 | 0.14 | 0.08 |
| 25 | 0.56 | 0.49 | 0.37 | 0.31 | 0.25 | 0.15 | 0.07 |
| 50 | 0.61 | 0.53 | 0.44 | 0.37 | 0.28 | 0.16 | 0.08 |
| 100 | 0.78 | 0.71 | 0.50 | 0.39 | 0.30 | 0.18 | 0.09 |

EXAMPLE 4

The experimental procedure was the same as in the preceding examples except that the electrode plates were prepared with a powder mixture of 100 parts by weight of the same titanium hydride, 10 parts by weight of the same silver chloride and 10 parts by weight of a reagent grade sodium tungstate dihydrate. The results are summarized in Table 6.

TABLE 6

| Electrode pair No. | Potential Difference between Electrodes, mV | | | | | |
|---|---|---|---|---|---|---|
| | Initial | After 1 min. | After 10 mins. | After 30 mins. | After 1 hr. | After 10 hrs. | After 24 hrs. |
| 1 | 0.72 | 0.67 | 0.53 | 0.35 | 0.20 | 0.11 | 0.07 |
| 2 | 0.54 | 0.57 | 0.45 | 0.36 | 0.24 | 0.13 | 0.08 |
| 3 | 0.88 | 0.85 | 0.57 | 0.39 | 0.26 | 0.14 | 0.08 |
| 4 | 0.55 | 0.48 | 0.40 | 0.37 | 0.28 | 0.17 | 0.12 |
| 5 | 0.57 | 0.52 | 0.46 | 0.36 | 0.27 | 0.16 | 0.11 |
| 6 | 0.53 | 0.49 | 0.42 | 0.30 | 0.22 | 0.12 | 0.09 |
| 7 | 0.35 | 0.37 | 0.30 | 0.15 | 0.12 | 0.07 | 0.05 |
| 8 | 0.60 | 0.57 | 0.38 | 0.18 | 0.15 | 0.11 | 0.06 |
| 9 | 0.10 | −0.46 | −0.24 | −0.12 | −0.11 | −0.09 | 0.04 |
| 10 | 0.62 | 0.61 | 0.43 | 0.38 | 0.25 | 0.11 | 0.06 |

The electrode plates prepared in this example and in Example 2 were each placed on a glass dish and gently heated from beneath the dish to test the formation of hydrogen chloride by fuming of ammonium chloride when a glass rod wet with ammonia water was brought near to react with the hydrogen chloride, if present. In the case of the electrode plate prepared in this example, no fuming was detected while considerable fuming was observed for the electrode plate prepared in Example 2 showing the formation of hydrogen chloride.

Further, the electrode plates prepared in this example and in Example 2 were each dipped in 10 ml of distilled water and the pH of the water was determined over a period of 24 hours and the results are shown in FIG. 3 with the value of pH as the ordinate and the time in hours as the abscissa, in which Curve (a) is for the electrode plate of this example and Curve (b) is for the electrode plate of Example 2. The results clearly indicate the formation of hydrochloric acid in the electrode plate of Example 2.

EXAMPLE 5

Electrode plates were prepared in the same manner as in Example 4 excepting the use of one of the other basic metal salts of group A given in Table 1 instead of sodium tungstate used in Example 4. The characteristics of electrode potential of the electrodes for living body with these electrode plates were examined in the same manner as in Example 1 to give the results set out in Table 7 below giving the average values of millivolts obtained with 10 pairs of the electrodes for each of the basic salt additives.

TABLE 7

| | Potential Difference between Electrodes, mV | | | | | | |
|---|---|---|---|---|---|---|---|
| Additive | Initial | After 1 min. | After 10 mins. | After 30 mins. | After 1 hr. | After 10 hrs. | After 24 hrs. |
| Calcium tungstate | 1.12 | 0.95 | 0.62 | 0.40 | 0.16 | 0.07 | 0.02 |
| Magnesium tungstate | 1.68 | 1.40 | 0.88 | 0.62 | 0.37 | 0.10 | 0.05 |
| Sodium molybdate | 1.25 | 1.13 | 0.64 | 0.57 | 0.22 | 0.09 | 0.05 |
| Calcium molybdate | 0.88 | 0.82 | 0.63 | 0.39 | 0.15 | 0.08 | 0.04 |
| Magnesium molybdate | 1.61 | 1.54 | 0.86 | 0.68 | 0.30 | 0.14 | 0.09 |
| Calcium silicate | 1.16 | 1.12 | 0.74 | 0.51 | 0.23 | 0.11 | 0.05 |
| Magnesium silicate | 1.25 | 1.02 | 0.73 | 0.47 | 0.30 | 0.27 | 0.11 |
| Calcium metasilicate | 0.70 | 0.72 | 0.48 | 0.29 | 0.24 | 0.10 | 0.03 |
| Magnisium metasilicate | 0.99 | 0.84 | 0.56 | 0.33 | 0.15 | 0.12 | 0.06 |
| Lithium tetraborate | 0.74 | 0.74 | 0.44 | 0.29 | 0.22 | 0.16 | 0.08 |
| Sodium tetraborate | 0.85 | 0.79 | 0.59 | 0.36 | 0.19 | 0.15 | 0.04 |
| Potassium tetraborate | 0.82 | 0.83 | 0.61 | 0.46 | 0.29 | 0.18 | 0.07 |
| Calcium tetraborate | 0.93 | 0.86 | 0.59 | 0.38 | 0.14 | 0.08 | 0.03 |
| Magnesium tetraborate | 0.95 | 0.93 | 0.72 | 0.54 | 0.22 | 0.16 | 0.10 |

EXAMPLE 6

Electrode plates were prepared in the same manner as in Example 4 except that the amounts of the silver chloride and the sodium tungstate were not 10 parts by weight each but varied in three levels of 5, 25 and 50 parts by weight per 100 parts by weight of the titanium hydride to give 9 different compositions.

The characteristics of electrode potential of the electrodes for living body with the thus prepared electrode plates were examined in the same manner as in Example 1 to give the results set out in Table 8 below giving the average values of millivolts obtained with 10 pairs of the electrodes for each of the 9 compositions.

EXAMPLE 7

The experimental procedure was the same as in the preceding examples except that the electrode plates were prepared with a powder mixture composed of 100 parts by weight of the same titanium hydride, 10 parts by weight of the same silver chloride, 10 parts by weight of the same sodium tungstate dihydrate and 5 parts by weight of a graphite powder. The results are summarized in Table 9 below.

TABLE 8

| TiH$_2$, Parts by weight | AgCl, Parts by weight | Na$_2$WO$_4$, Parts by weight | Exp. No. | Potential Difference between Electrodes, mV | | | | | | |
|---|---|---|---|---|---|---|---|---|---|---|
| | | | | Initial | After 1 min. | After 10 mins. | After 30 mins. | After 1 hr. | After 10 hrs. | After 24 hrs. |
| | | 5 | 1 | 0.83 | 0.67 | 0.45 | 0.26 | 0.11 | 0.04 | 0.02 |
| | 5 | 25 | 2 | 1.14 | 1.07 | 0.69 | 0.48 | 0.20 | 0.08 | 0.03 |
| | | 50 | 3 | 1.40 | 1.35 | 0.82 | 0.63 | 0.24 | 0.11 | 0.07 |
| | | 5 | 4 | 0.65 | 0.72 | 0.33 | 0.24 | 0.17 | 0.04 | 0.01 |
| 100 | 25 | 25 | 5 | 0.66 | 0.61 | 0.52 | 0.25 | 0.14 | 0.07 | 0.02 |
| | | 50 | 6 | 0.81 | 0.76 | 0.45 | 0.32 | 0.18 | 0.15 | 0.04 |
| | | 5 | 7 | 0.75 | 0.74 | 0.40 | 0.23 | 0.08 | 0.03 | 0.01 |
| | 50 | 25 | 8 | 0.84 | 0.81 | 0.53 | 0.27 | 0.12 | 0.05 | 0.03 |
| | | 50 | 9 | 0.92 | 0.88 | 0.64 | 0.31 | 0.15 | 0.10 | 0.04 |

TABLE 9

| Electrode pair No. | Potential Difference between Electrodes, mV | | | | | | |
|---|---|---|---|---|---|---|---|
| | Initial | After 1 min. | After 10 mins. | After 30 mins. | After 1 hr. | After 10 hrs. | After 24 hrs. |
| 1 | 0.47 | 0.44 | 0.34 | 0.26 | 0.19 | 0.13 | 0.07 |
| 2 | 0.82 | 0.75 | 0.41 | 0.28 | 0.22 | 0.16 | 0.08 |
| 3 | 0.14 | 0.11 | −0.25 | −0.18 | −0.13 | −0.05 | −0.06 |
| 4 | 0.85 | 0.84 | 0.62 | 0.39 | 0.30 | 0.17 | 0.11 |
| 5 | 0.24 | 0.27 | 0.25 | 0.16 | 0.12 | 0.09 | 0.07 |
| 6 | 0.78 | 0.74 | 0.53 | 0.31 | 0.25 | 0.16 | 0.09 |
| 7 | 0.66 | 0.59 | 0.45 | 0.27 | 0.16 | 0.10 | 0.10 |
| 8 | 0.93 | 0.78 | 0.60 | 0.48 | 0.25 | 0.15 | 0.09 |
| 9 | 0.12 | 0.21 | 0.25 | 0.23 | 0.18 | 0.16 | 0.12 |
| 10 | 0.55 | 0.57 | 0.38 | 0.26 | 0.21 | 0.14 | 0.06 |

The voltage-current characteristics of the elctrodes for living body were measured by applying DC voltage and the results are shown in FIG. 4, in which Curves (a) to (e) are for a conventional nickel silver electrode and the electrodes prepared in Example 1, Example 2, Example 4 and this example of the present invention, respectively. As is evident from this figure, all of the inventive electrodes are very superior to the conventional electrode and the electrode of this example is particularly excellent showing the advantage of the addition of the graphite powder.

EXAMPLE 8

The experimental procedure was the same as in Example 7 except that the amounts of silver chloride, sodium tungstate dihydrate and graphite powder were varied as indicated in Table 10 below.

The results are summarized in the same table, in which each of the numerical values is an average for 10 pairs of the electrodes prepared with the same formulation.

TABLE 10

| Amount of Additive, parts by weight per 100 parts by weight of titanium hydride | | | Potential Difference between Electrodes, mV | | | | | | |
|---|---|---|---|---|---|---|---|---|---|
| Silver chloride | Sodium tungstate dihydrate | Graphite powder | Initial | After 1 min. | After 10 mins. | After 30 mins. | After 1 hr. | After 10 hrs. | After 24 hrs. |
| 5 | 2 | 1 | 0.67 | 0.64 | 0.42 | 0.31 | 0.26 | 0.15 | 0.10 |
| 25 | 10 | 5 | 0.56 | 0.55 | 0.33 | 0.23 | 0.18 | 0.13 | 0.07 |
| 50 | 25 | 10 | 0.64 | 0.62 | 0.43 | 0.33 | 0.25 | 0.18 | 0.11 |

EXAMPLE 9

The experimental procedure was the same as in Example 7 except that the sodium tungstate used in Example 7 was replaced with either one of the other basic metal salts of group A given in Table 1.

The results are summarized in Table 11 below, in which each of the numerical values is an average for 10 pairs of the electrodes prepared with the same formulation.

EXAMPLE 10

Electrocardiograms were taken with several kinds of the electrodes for living body as shown in FIG. 5, in which the electrodardiogram (a) is for a conventional nickel silver electrode and electrocardiograms (b) to (e) are for the electrodes prepared in Example 1, Example 2, Example 4 and Example 7, respectively, of the present invention.

In each of the electrocardiograms (a) to (e), the left side is for a patient at rest and the right side is for the same patient under a load of running exercise. As is evident from this measurement, the electrodes of the present invention can give much better results, especially, when the patient is under a load.

TABLE 11

| | Potential Difference between Electrodes, mV | | | | | | |
|---|---|---|---|---|---|---|---|
| Additive | Initial | After 1 min. | After 10 mins. | After 30 mins. | After 1 hr. | After 10 hrs. | After 24 hrs. |
| Calcium tungstate | 0.78 | 0.75 | 0.46 | 0.30 | 0.18 | 0.05 | 0.03 |
| Magnesium tungstate | 0.94 | 0.90 | 0.62 | 0.58 | 0.24 | 0.11 | 0.07 |
| Sodium molybdate | 0.72 | 0.71 | 0.42 | 0.27 | 0.15 | 0.04 | 0.02 |
| Calcium molybdate | 0.83 | 0.84 | 0.50 | 0.34 | 0.23 | 0.09 | 0.05 |
| Magnesium molybdate | 0.98 | 0.92 | 0.58 | 0.45 | 0.23 | 0.14 | 0.08 |
| Calcium silicate | 1.16 | 1.14 | 0.75 | 0.65 | 0.44 | 0.25 | 0.11 |
| Magnesium silicate | 1.25 | 1.14 | 0.83 | 0.69 | 0.48 | 0.26 | 0.14 |
| Calcium metasilicate | 0.81 | 0.78 | 0.47 | 0.31 | 0.17 | 0.09 | 0.04 |
| Magnesium metasilicate | 0.82 | 0.81 | 0.52 | 0.33 | 0.19 | 0.13 | 0.09 |
| Lithium tetraborate | 0.97 | 0.95 | 0.68 | 0.57 | 0.30 | 0.17 | 0.12 |
| Sodium tetraborate | 0.88 | 0.87 | 0.48 | 0.35 | 0.21 | 0.11 | 0.06 |
| Potassium tetraborate | 1.05 | 0.99 | 0.58 | 0.43 | 0.25 | 0.12 | 0.08 |
| Calcium tetraborate | 0.92 | 0.93 | 0.55 | 0.41 | 0.27 | 0.15 | 0.10 |
| Magnesium tetraborate | 1.03 | 0.98 | 0.64 | 0.42 | 0.28 | 0.17 | 0.13 |

What is claimed is:

1. In an electrode for the living body comprising a dish-like casing of an electrically insulating material and an electrode plate fixed to the casing at the cavity thereof, the lower surface of the electrode plate being exposed bare and a lead wire being connected to the upper surface of the electrode plate, the improvement that the electrode plate is formed of titanium hydride admixed with a silver halide, the silver halide being admixed with the titanium hydride in an amount from 1 to 100 parts by weight per 100 parts by weight of the titanium hydride.

2. In the electrode for living body according to claim 1, the improvement that the electrode plate is formed of titanium hydride admixed with a silver halide and a basic salt of a metal.

3. In the electrode for living body according to claim 2, the improvement that the silver halide and the basic salt of a metal are admixed to the titanium hydride in amounts from 1 to 100 parts by weight and from 1 to 50 parts by weight, respectively, per 100 parts by weight of the titanium hydride.

4. In the electrode for living body according to claim 1, the improvement that the electrode plate is formed of titanium hydride admixed with a silver halide, a basic salt of a metal and a carbon powder.

5. In the electrode for living body according to claim 2, or claim 4, the improvement that the basic salt of a metal is selected from the group consisting of tungstates, molybdates, sulfites, phosphates, pyrophosphates, hypophosphites, metaphosphates, silicates, metasilicates, tetraborates and metaborates of lithium, sodium, potassium, calcium or magnesium.

6. In the electrode for living body according to claim 2 or claim 4, the improvement that the basic salt of a metal is selected from the group consisting of tungstates of sodium, calcium and magnesium, molybdates of sodium, calcium and magnesium, silicates of calcium and magnesium, metasilicates of calcium and magnesium and tetraborates of lithium, sodium, potassium, calcium and magnesium.

7. In the electrode for living body according to claim 4, the improvement that the silver halide, the basic salt of a metal and the carbon powder are admixed to the titanium hydride in amounts from 1 to 100 parts by weight, from 1 to 50 parts by weight and from 1 to 20 parts by weight, respectively, per 100 parts by weight of the titanium hydride.

8. In the electrode for living body according to claim 4, the improvement that the carbon powder is a graphite powder.

9. In the electrode for living body according to claim 2, 4, 3 or 7, the improvement that the silver halide is silver chloride.

10. In the electrode for living body according to claim 1, the improvement that the titanium hydride has a degree of hydrogenation of approximately 2.

11. In an electrode for the living body comprising a support and an electrode plate fixed to the support, a surface of the electrode plate being exposed bare, relative to the support for engagement with the body, and means for electrically connecting the electrode plate to a terminal, the improvement that the electrode plate is formed from a material comprising at least 50% by weight of titanium hydride.

* * * * *